United States Patent
Rice et al.

(10) Patent No.: US 8,496,636 B2
(45) Date of Patent: Jul. 30, 2013

(54) SYSTEM AND METHOD FOR UNFOLDING AND DISPENSING DIAPERS

(75) Inventors: Jonathan K. Rice, Evans, GA (US);
Walter C. Reade, Appleton, WI (US);
Daniel L. Ellingson, Appleton, WI (US);
Rhonda K. Joch, Fremont, WI (US);
Brenda M. Nelson, Appleton, WI (US);
Denise J. Nelson, Hortonville, WI (US);
Jaime M. Vitense, Appleton, WI (US);
Timothy P. Clare, Appleton, WI (US);
Connie J. Warshall, Harshaw, WI (US);
John P. Vukos, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 995 days.

(21) Appl. No.: 11/970,363

(22) Filed: Jan. 7, 2008

(65) Prior Publication Data

US 2008/0105635 A1    May 8, 2008

Related U.S. Application Data

(62) Division of application No. 11/020,453, filed on Dec. 22, 2004.

(51) Int. Cl.
*A61F 13/15* (2006.01)
(52) U.S. Cl.
USPC .............................. 604/385.02; 604/385.201
(58) Field of Classification Search
USPC ..................... 604/385.02, 385.201
See application file for complete search history.

(56) References Cited

U.S. PATENT DOCUMENTS

| | | | | |
|---|---|---|---|---|
| 1,688,242 A | * | 10/1928 | Frank et al. | 221/34 |
| 3,747,802 A | * | 7/1973 | Uroshevich | 221/63 |
| 4,199,068 A | | 4/1980 | Weitzner | |
| 4,598,528 A | * | 7/1986 | McFarland et al. | 53/430 |
| 4,623,074 A | * | 11/1986 | Dearwester | 221/48 |
| 4,706,845 A | * | 11/1987 | Schnurer et al. | 221/102 |
| 5,443,161 A | * | 8/1995 | Jonese | 206/581 |
| 5,666,787 A | * | 9/1997 | Young et al. | 53/438 |
| 5,678,727 A | | 10/1997 | Rice | |
| 5,735,433 A | | 4/1998 | Power | |
| 5,971,153 A | * | 10/1999 | Bauer et al. | 206/494 |
| 6,412,652 B1 | | 7/2002 | Woram et al. | |

(Continued)

FOREIGN PATENT DOCUMENTS

| EP | 0947446 A1 | 10/1999 |
|---|---|---|
| WO | WO-2006071320 A1 | 7/2006 |

OTHER PUBLICATIONS

Non-Final Office Action mailed Jul. 27, 2007 in U.S. Appl. No. 11/020,453, OARN, 9 pages.

*Primary Examiner* — Lynne Anderson
(74) *Attorney, Agent, or Firm* — Dority & Manning, P.A.

(57) ABSTRACT

The present invention relates to a system for unfolding and dispensing diapers. The system includes a dispenser and a folded diaper that is within the dispenser. The folded diaper includes a first longitudinal fold that is between a main portion and a first side portion and a second longitudinal fold that is between the main portion and a second side portion. The dispenser includes a first projection that unfolds the first longitudinal fold as the diaper is removed from the dispenser and a second projection that unfolds the second longitudinal fold as the diaper is removed from the dispenser. The system may make it easier for care givers to perform multiple diaper changes per day.

8 Claims, 10 Drawing Sheets

U.S. PATENT DOCUMENTS

| | | |
|---|---|---|
| 6,540,103 B2 | 4/2003 | Silvers |
| 6,543,639 B1 | 4/2003 | Kovens |
| 2003/0006244 A1 | 1/2003 | Silvers |
| 2003/0102239 A1* | 6/2003 | Beard .......................... 206/440 |
| 2006/0135935 A1 | 6/2006 | Rice et al. |

* cited by examiner

70

72

GRASPING A FOLDED DIAPER THAT IS AT LEAST
PARTIALLY WITHIN A DISPENSER

- GRASPING THE FOLDED DIAPER WHEN THE FOLDED DIAPER IS ENTIRELY WITHIN THE DISPENSER
- GRASPING THE FOLDED DIAPER WITH A HAND
- THE FOLDED DIAPER INCLUDES A FIRST SECTION AND A SECOND SECTION WITH A LATERAL FOLD BETWEEN THE FIRST SECTION AND THE SECOND SECTION, GRASPING ONE OF THE FIRST AND SECOND SECTIONS
- THE FOLDED DIAPER INCLUDES A FIRST LONGITUDINAL FOLD THAT IS BETWEEN A MAIN PORTION AND A FIRST SIDE PORTION AND A SECOND LONGITUDINAL THAT IS BETWEEN THE MAIN PORTION AND A SECOND SIDE PORTION, GRASPING THE MAIN PORTION OF THE DIAPER

74

REMOVING THE FOLDED DIAPER FROM A DISPENSER
SUCH THAT THE DISPENSER UNFOLDS THE DIAPER

- REMOVING THE FOLDED DIAPER FROM A STACK OF FOLDED DIAPERS WITHIN THE DISPENSER
- REMOVING THE FOLDED DIAPER FORM A ROLL OF FOLDED DIAPERS WITHIN THE DISPENSER
- TEARING A PERFORATED SECTION THAT CONNECTS THE FOLDED DIAPER TO AT LEAST ONE OTHER FOLDED DIAPER THAT IS WITHIN THE DISPENSER
- THE FOLDED DIAPER INCLUDES A FIRST SECTION AND A SECOND SECTION WITH A LATERAL FOLD BETWEEN THE FIRST SECTION AND THE SECOND SECTION, UNFOLDING THE LATERAL FOLD BY ENGAGING THE DISPENSER WITH THE OTHER OF THE FIRST AND SECOND SECTIONS
- THE FOLDED DIAPER INCLUDES A FIRST LONGITUDINAL FOLD THAT IS BETWEEN A MAIN PORTION AND A FIRST SIDE PORTION AND A SECOND LONGITUDINAL FOLD THAT IS BETWEEN THE MAIN PORTION AND A SECOND SIDE PORTION, AND ENGAGING A FIRST PROJECTION ON THE DISPENSER WITH THE FOLDED DIAPER TO UNFOLD THE FIRST LONGITUDINAL FOLD AND ENGAGING A SECOND PROJECTION ON THE DISPENSER WITH THE FOLDED DIAPER TO UNFOLD THE SECOND LONGITUDINAL FOLD

FIG. 12

SYSTEM AND METHOD FOR UNFOLDING AND DISPENSING DIAPERS

RELATED APPLICATION

This patent application is a divisional under 37 C.F.R. 1.53(b) of U.S. patent application Ser. No. 11/020,453 filed Dec. 22, 2004, which is incorporated herein by reference and made a part hereof.

FIELD

Some embodiments of the invention relate to a system and method for dispensing diapers, and in particular to a system and method for unfolding and dispensing diapers.

BACKGROUND

Child care providers are typically required to change diapers many times per day. The high number of diaper changes requires care providers to stock a large number of diapers.

Diapers are commonly supplied to care givers in a package where the diapers are folded and then stacked one on top of another. One of the drawbacks with folding diapers within a package is that care providers are typically unable to efficiently access the diapers during diaper changes because the diapers must be unfolded before they are applied to a child. In addition, unfolding diapers before a diaper change requires a care giver to perform extra steps in order to get the diaper ready-to-use.

SUMMARY OF THE INVENTION

The present invention relates to a system and method for unfolding and dispensing diapers. The system and method may make it more convenient for care givers to perform multiple diaper changes per day. The system and method may also dispense diapers one at a time as needed for each diaper change. The system and method may also reduce the number of steps that are required for a care giver to change a diaper because the diapers are unfolded as they are removed from a dispenser.

In one aspect, the system for unfolding and dispensing diapers includes a dispenser and a folded diaper that is within the dispenser. The dispenser engages the diaper to unfold the diaper as the diaper is removed from the dispenser. In some embodiments, the diaper includes one or more lateral folds that are unfolded as the diaper is removed from the dispenser and/or one or more longitudinal folds that are unfolded as the diaper is removed from the dispenser.

The system may further include a plurality of folded diapers that are within the dispenser. The dispenser may engage each of the diapers to unfold the diapers as each diaper is removed from the dispenser. The plurality of diapers may be stacked one on top of another within the dispenser or be part of a roll of diapers.

In another aspect, the present invention relates to a method of unfolding and dispensing diapers. The method includes grasping a folded diaper that is at least partially within a dispenser and removing the folded diaper from the dispenser such that the dispenser unfolds the diaper. Unfolding the diapers as they are removed from the dispenser may make it easier for care providers to change diapers.

In some embodiments, grasping the folded diaper may include grasping the folded diaper with a hand while in other embodiments the diapers may be grasped by some type of mechanism that is part of the dispenser. In addition, removing the folded diaper from the dispenser may include tearing a perforated section that connects the diaper to at least one other diaper which is within the dispenser.

The purposes and features of the present invention will be set forth in the description that follows. Additional features of the invention may be realized and attained by the product and processes particularly pointed out in the written description and claims hereof, as well as from the appended drawings.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the invention.

BRIEF DESCRIPTION OF THE DRAWINGS

The present invention will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

FIG. 12 is a flow diagram illustrating a method of unfolding and dispensing diapers.

DETAILED DESCRIPTION OF THE INVENTION

In the following detailed description, reference is made to the accompanying drawings, which show specific embodiments in which the invention may be practiced. These embodiments are described in sufficient detail to enable those skilled in the art to practice the invention. It is to be understood that other embodiments may be utilized and structural changes made, such that the following detailed description is not to be taken in a limiting sense.

Figure 1:
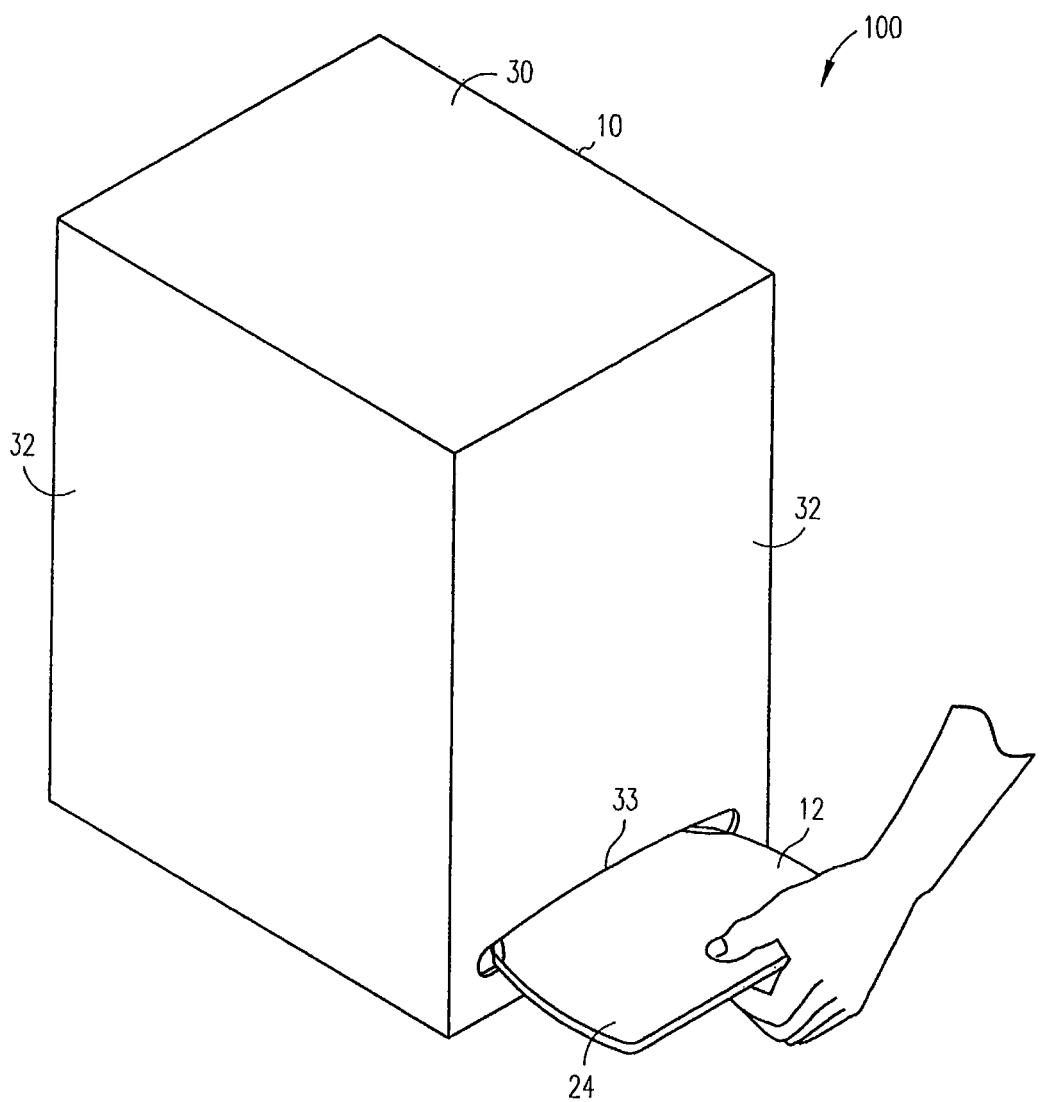
FIG. 1 is a schematic perspective view illustrating an example embodiment of a system for unfolding and dispensing diapers.
Figure 2:
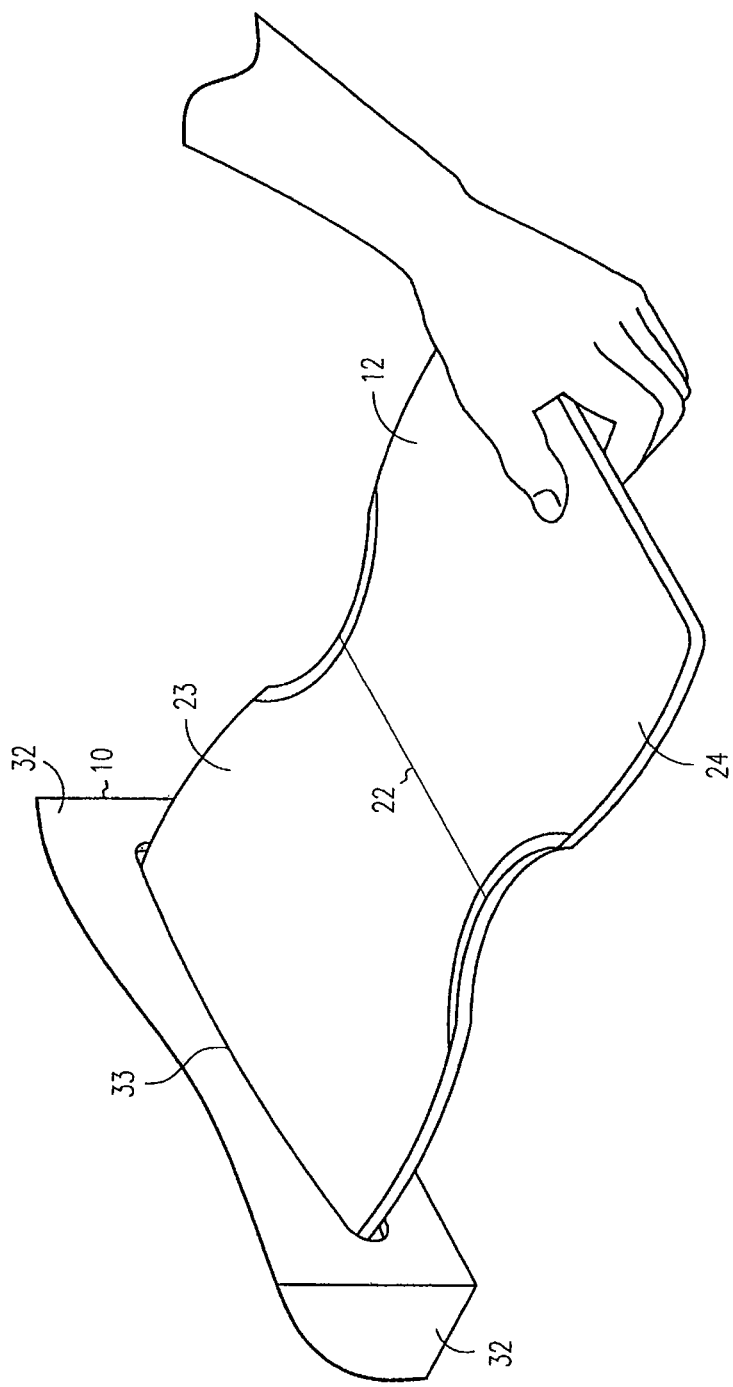
FIG. 2 is an enlarged view illustrating a portion of the system shown in FIG. 1.

FIGS. 1 and 2 illustrate an example system 100 for unfolding and dispensing diapers. The system 100 includes a dispenser 10 and a folded diaper 12 that is within the dispenser 10. The dispenser 10 engages the folded diaper 12 to unfold the diaper 12 as the diaper 12 is removed from the dispenser

10. As used herein, a diaper 12 "within" the dispenser 10 means containing, constraining, enclosing, holding, compressing, contacting or supporting the diaper 12 within, upon and/or against the dispenser 10 by any method.

Although FIG. 1 illustrates that a box may be used as dispenser 10, it should be noted that any type of storage device, disposable package or reusable container may used in system 100. Some other example dispensers 10 include cans, jars, racks, bags, pouches, cubbies, shelves, drawers, cupboards, closets, cabinets, crates, trunks, totes and/or tubs (among others).

The dispenser 10 may be disposable or reusable and may be plain or decorated in some manner. In addition, the dispenser 10 may be used as a shipping container or to perform some other function. It should be noted that dispenser 10 may be of any size, shape or material.

Any type of diaper 12 may be used in the system 100 or any of the systems described herein. Some example diapers include newborn diapers, premature baby diapers, overnight diapers and diapers of various other sizes. Other example diapers include specialized diapers, such as diapers for urine absorption, feces absorption, blood absorption, sweat absorption, menses absorption and diapers that apply a lotion or medication. The diapers may also be swim pants, training pants, diaper pants (PULLUPS®, EASY UPS®, GOODNIGHTS®) and absorbent underpants (among others).

Figure 3:
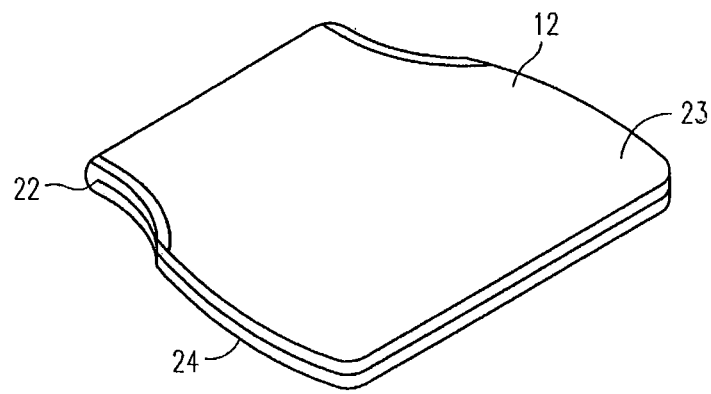
FIG. 3 shows an example folded diaper that may be used in the system shown in FIG. 1.
Figure 4:
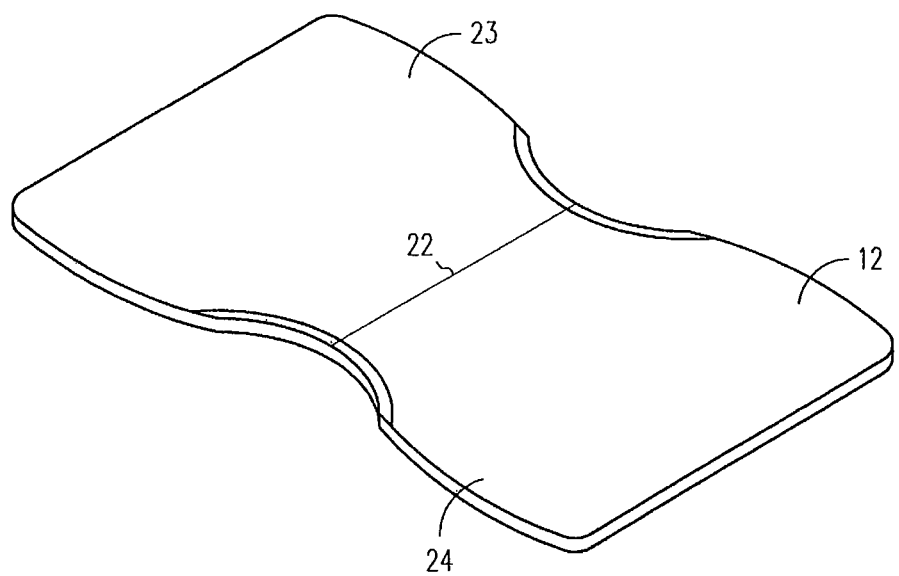
FIG. 4 shows the example folded diaper of FIG. 3 where the diaper is unfolded.

As shown also in FIGS. 3 and 4, the diaper 12 may include a lateral fold 22 that is unfolded as the diaper 12 is removed from the dispenser 10. The diaper 12 may further include a first section 23 and a second section 24 such that the lateral fold 22 separates the first and second sections 23, 24. The dispenser engages one of the first and second sections 23, 24 to unfold the lateral fold 22 as the diaper 12 is removed from the dispenser 10. First section 23 is not visible in FIG. 1 because dispenser 10 is engaging first section 23 inside dispenser 10 to unfold the diaper 12.

In the example embodiment illustrated in FIGS. 1 and 2, the dispenser 10 includes a top wall 30 and a bottom wall (not visible in FIGS. 1 and 2). The top wall 30 and the bottom wall are connected together by a plurality of side walls 32. The dispenser 10 may also include an opening 33 in one of the side walls 32 such that the diaper 12 is removed from the dispenser 10 through the opening 33.

As discussed above, the dispenser may be any type of shape as long as the dispenser 10 is able to hold a folded diaper 12. It should be noted that the opening 33 may have any size or shape that promotes unfolding and dispensing diapers 12. In addition, the opening 33 may be anywhere in dispenser 10. The shape of the opening 33 will depend in large part on the size, shape and type of folds that are in the diaper 12.

Figure 5:
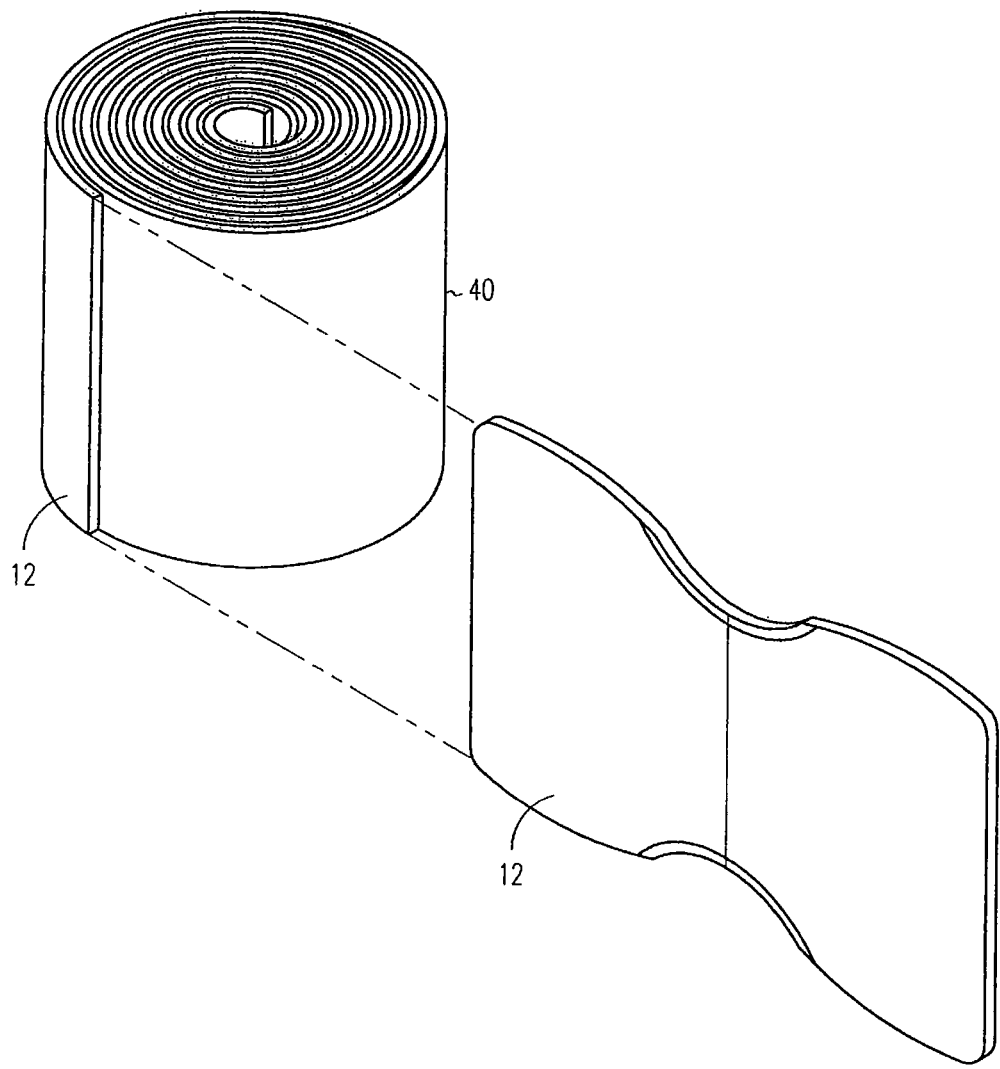
FIG. 5 shows an example of a plurality of folded diapers that may be used in the system shown in FIG. 1.
Figure 6:
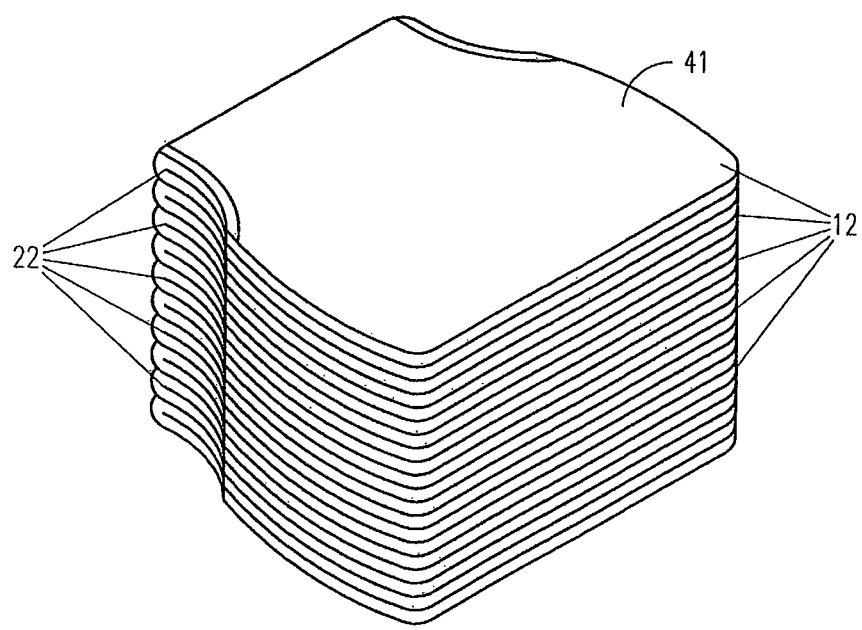
FIG. 6 shows another example of a plurality of folded diapers that may be used in the system shown in FIG. 1.
Figure 7:
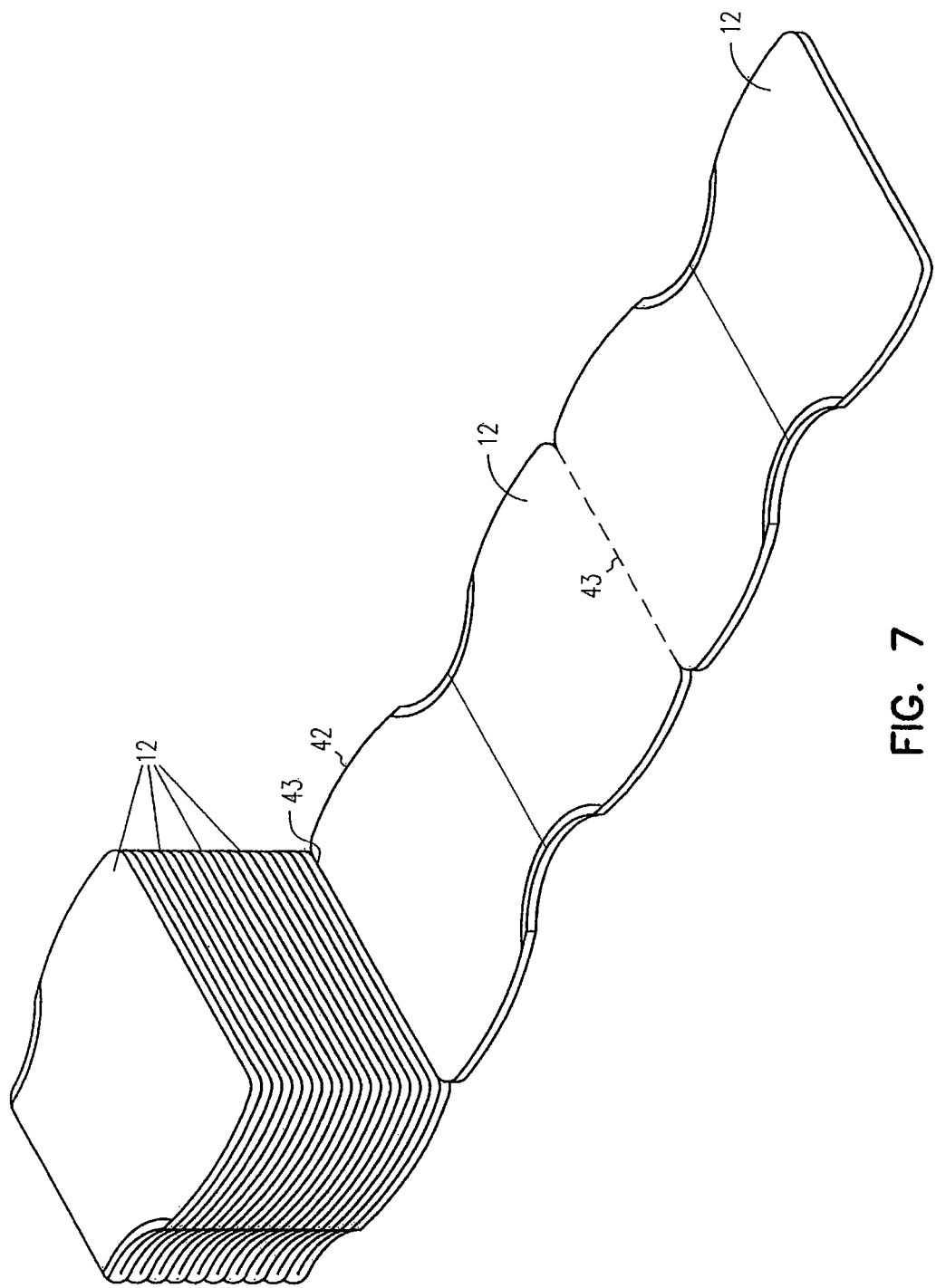
FIG. 7 shows yet another example of a plurality of folded diapers that may be used in the system shown in FIG. 1.

The system 100 may further include a plurality of folded diapers 12 that are within the dispenser 10 (see, e.g., FIGS. 5-7). The dispenser 10 engages each of the folded diapers 12 to unfold the diapers 12 as each diaper 12 is removed from the dispenser 10.

The diapers 12 may be dispensed from a roll 40 (FIG. 5) or a stack 41 (FIG. 6) depending on the application where the system 100 is being used. As an example, the diapers 12 may be stacked so that the waistbands of the diapers 12 are facing the opening 33. In addition, the diapers 12 may be interfolded such that the next folded diaper 12 "pops through" through the opening 33 as one of the diapers 12 is removed from the dispenser 10. The folded diapers 12 may be stacked within the dispenser 10 in a variety of ways to facilitate being removed through the opening 33.

It should be noted that the dispenser 10 and/or the opening 33 may be designed in any configuration as long as the diapers 12 unfold when they are removed from the dispenser 10. In some embodiments, the dispenser 10 may include an unfolding mechanism (not shown) that unfolds the diapers 12 as the diapers 12 are removed from the dispenser 10. As used herein, "unfolding mechanism" includes any unfolding mechanisms that are known now or discovered in the future.

In some embodiments, the folded diapers 12 may be stacked on a spring-loaded platform (not shown) that is within the dispenser 10. The spring loaded platform may be designed to lift the remaining diapers 12 as one of the diapers 12 is removed from the dispenser 10.

The dispenser 10 may also include an access point (not shown) that is separate from the opening 33. The access point may allow a care giver to remove some folded diapers 12 from the dispenser 10 without having to pull the folded diapers 12 through the opening 33. Therefore, a care giver may be able to bypass the unfolding process when the care giver wants to transport some folded diapers 12 to another location.

As shown in FIG. 7, the folded diapers 12 may be part of a web 42 that includes perforated sections 43. When the folded diapers 12 are removed from the dispenser 10, the diapers 12 may be removed from the rest of the web 42 by tearing at least one of the perforated sections 43. The ability to supply the diapers 12 as a web 42 eliminates the need to separate the folded diapers 12 during high volume diaper manufacturing.

The perforated sections 43 may allow a portion of the next diaper 12 to be pulled through the opening 33 when one of the diapers 12 is removed from the dispenser 10. It should be noted that the dispenser 10 may include serrations (not shown) at the opening 33 to facilitate tearing the perforated sections 43 of the web 42 as the diapers 12 are removed from the dispenser 10.

Figure 8:
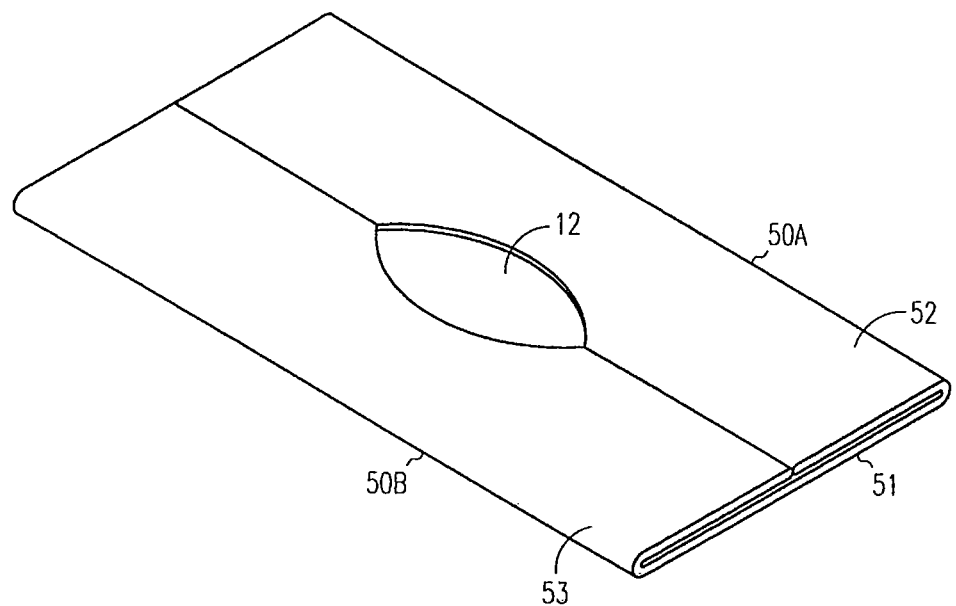
FIG. 8 shows another example folded diaper that may be used in the system shown in FIG. 1.
Figure 9:
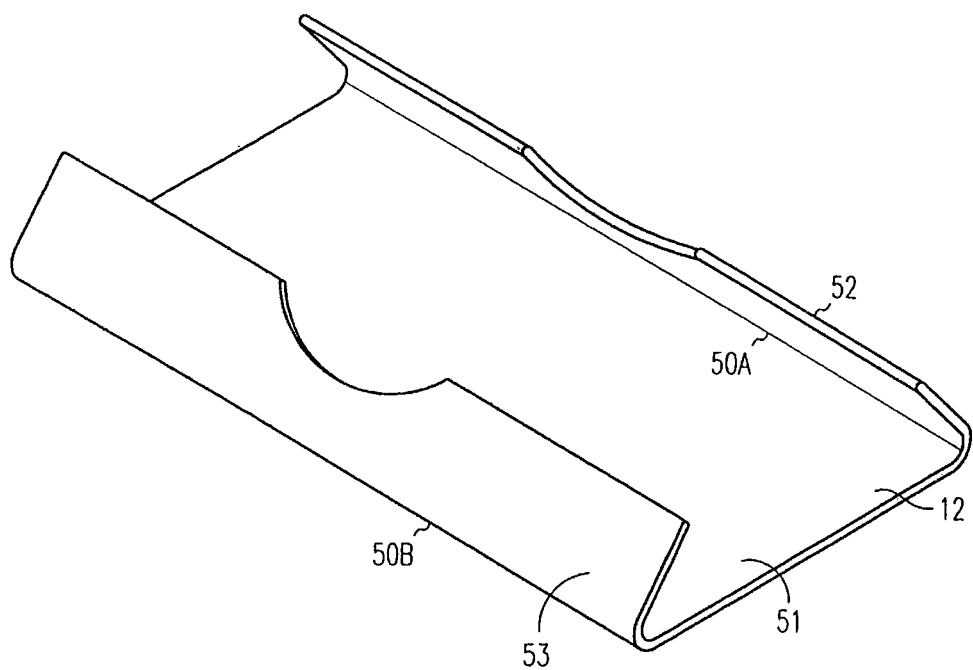
FIG. 9 shows the example folded diaper of FIG. 8 where the diaper is unfolded.

FIGS. 8 and 9 show another example folded diaper 12 that may be used in the system 100. The example folded diaper 12 includes one or more longitudinal folds that are unfolded as each diaper 12 is removed from the dispenser 10.

In the example embodiment illustrated in FIGS. 8 and 9, the folded diaper 12 includes a main portion 51 that is between a first side portion 52 and a second side portion 53. A first longitudinal fold 50A is between the main portion 51 and the first side portion 52 and a second longitudinal fold 50B is between the main portion 51 and the second side portion 53. A comparison of FIGS. 3 and 4 with FIGS. 8 and 9 illustrates the differences between lateral folds and longitudinal folds on diapers.

Figure 10:
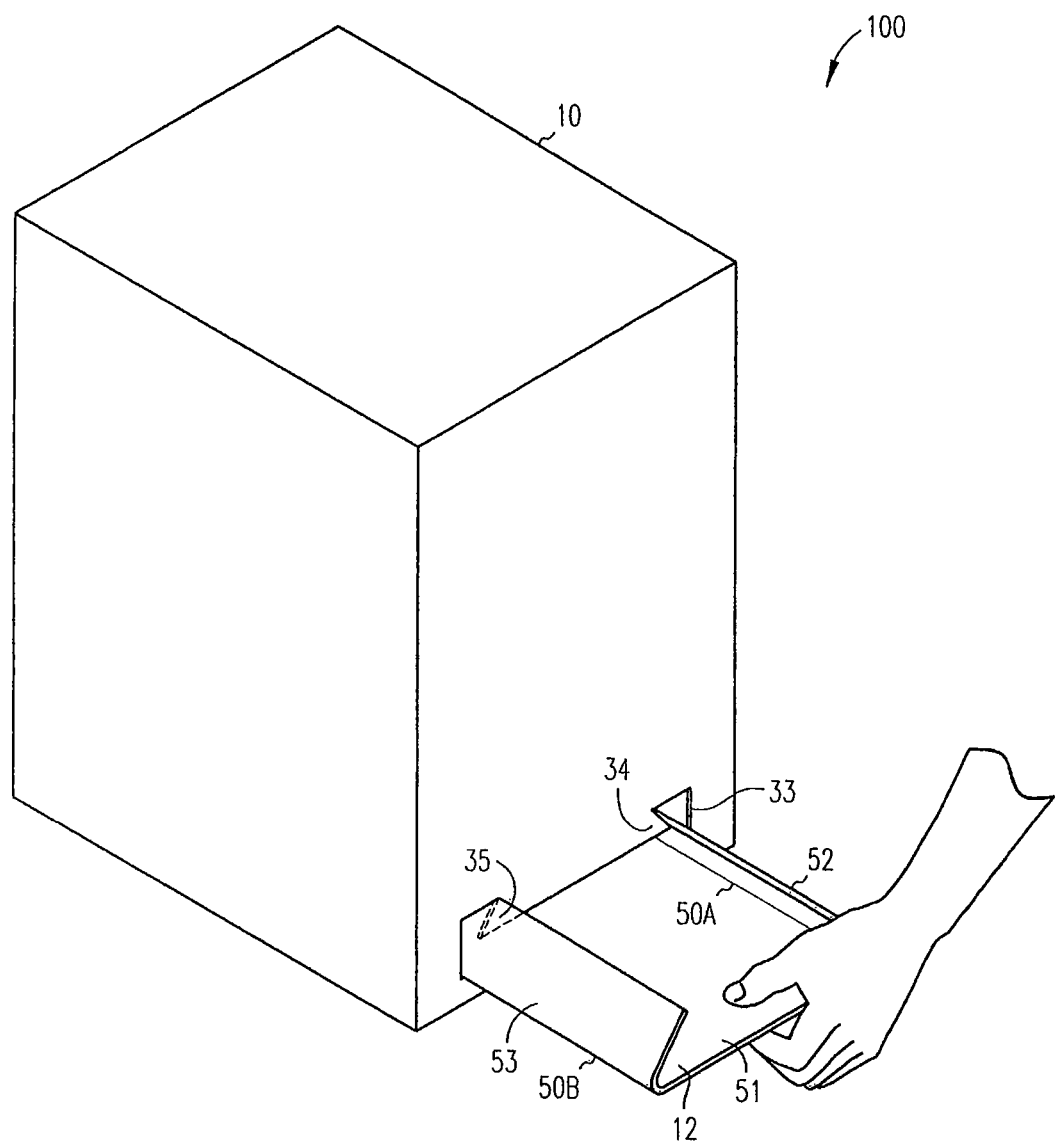
FIG. 10 is a schematic perspective view illustrating another example embodiment of the system for unfolding and dispensing diapers.
Figure 11:
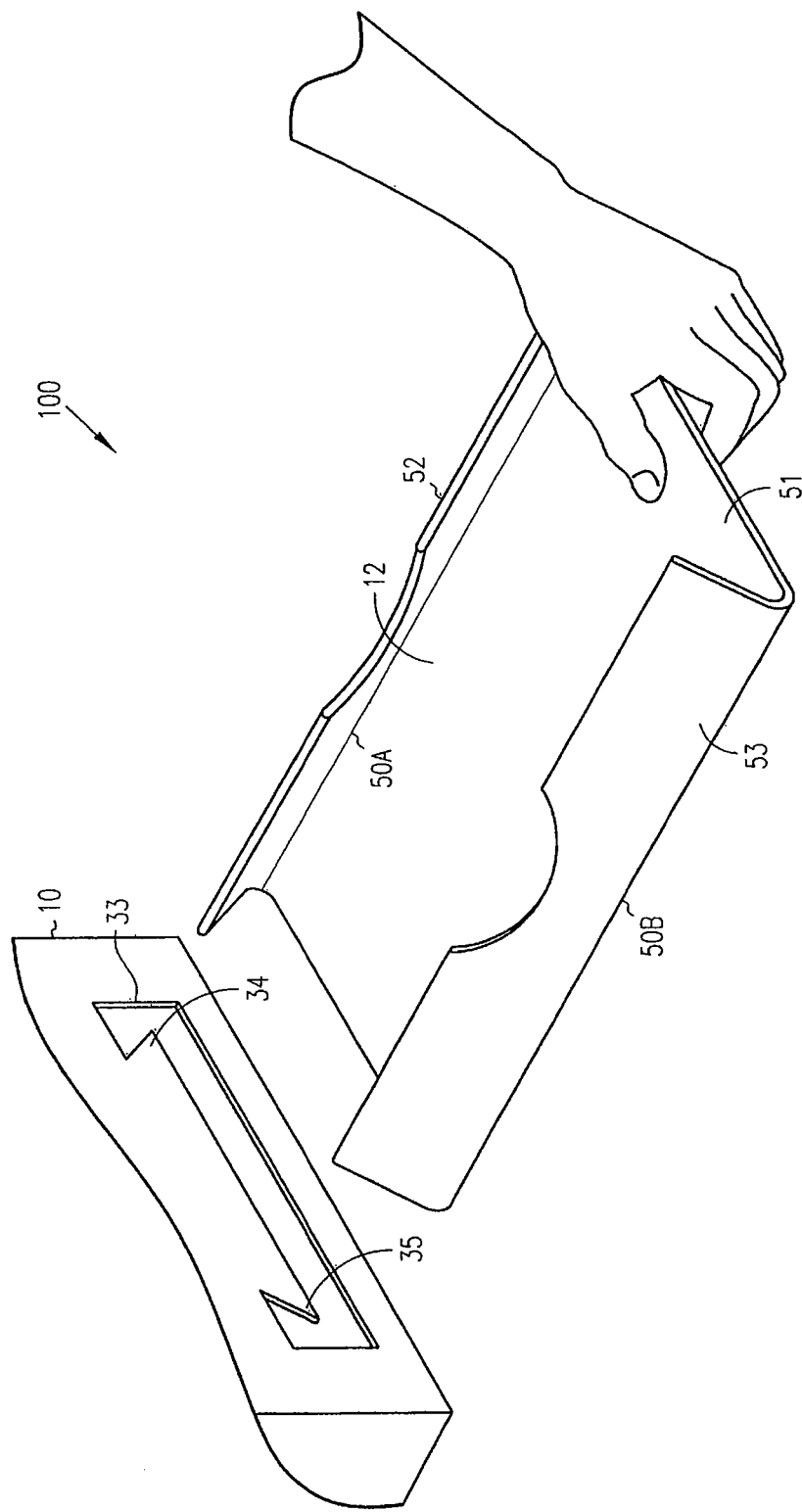
FIG. 11 is an enlarged view illustrating a portion of the system shown in FIG. 10.

FIGS. 10 and 11 illustrate an example embodiment where the system 100 includes a folded diaper 12 that is similar to the folded diaper 12 shown in FIGS. 8 and 9. The dispenser 10 includes a first projection 34 at the opening 33. The first projection 34 unfolds the first longitudinal fold 50A as the diaper 12 is removed from the dispenser 10.

The dispenser 10 further includes a second projection 35 at the opening 33. The second projection 35 unfolds the second longitudinal fold 50B as the diaper 12 is removed from the dispenser 10.

It should be noted that the dispenser 10 may include projections of any number, size or shape at the opening 33. The number, size and shape of the projections will depend in large part on the size, shape and type of folds that are in the diaper 12.

In some embodiments, one or more of the diapers 12 may include a fastener (not shown) that is folded when the diapers 12 are within the dispenser 10. The dispenser 10 may serve to unfold any fasteners (e.g., a hook-and-loop type fastener) that are part of the diapers 12 as the diapers 12 are removed from the dispenser 10.

A method 70 of unfolding and dispensing diapers is described herein with reference to FIG. 12. The method 70 includes grasping a folded diaper that is at least partially within a dispenser 72 (see, e.g., the hand shown in FIGS. 1-2 and 10-11). The method further includes removing the folded diaper from the dispenser such that the dispenser unfolds the diaper 74. Unfolding the diaper as the diaper is dispensed places the diaper in a "ready to use" condition for a diaper change.

It should be noted that grasping a folded diaper that is at least partially within a dispenser 72 may include grasping the folded diaper when the folded diaper is entirely within the dispenser. In addition, grasping a folded diaper that is at least partially within a dispenser 72 may include grasping the folded diaper with a hand or some other mechanism that is part of the dispenser.

In some embodiments, removing the folded diaper from the dispenser such that the dispenser unfolds the diaper 74 may include removing the diaper from a stack of diapers (see FIG. 5) within the dispenser or removing the diaper from a roll of diapers (see FIG. 6) within the dispenser. In addition, removing the folded diaper from the dispenser 72 may include tearing a perforated section that connects the folded diaper to at least one other folded diaper within the dispenser (see, e.g., perforated sections 43 in FIG. 7). The perforated sections may allow a portion of the next folded diaper to emerge from the dispenser after a diaper is removed from the dispenser.

Any type of folded diaper may be used in the method 70 of the present invention. As an example, the diaper may include a lateral fold that is between a first section and a second section (see, e.g., diaper 12 in FIGS. 3 and 4) such that grasping the folded diaper 72 may include grasping one of the first and second sections. In addition, removing the folded diaper from the dispenser 74 may include unfolding the lateral fold by engaging the dispenser with the other of the first and second sections (see, e.g., FIGS. 1 and 2).

As another example, the folded diaper may include a first longitudinal fold that is between a main portion and a first side portion and a second longitudinal fold that is between the main portion and a second side portion (see, e.g., diaper 12 in FIGS. 8 and 9) such that grasping the folded diaper 72 may include grasping the main portion of the diaper (see, e.g., FIGS. 10 and 11). In addition, removing the folded diaper from the dispenser 72 may include (i) engaging a first projection on the dispenser with the folded diaper to unfold the first longitudinal fold; and (ii) engaging a second projection on the dispenser with the folded diaper to unfold the second longitudinal fold.

The operations discussed above with respect to the described methods may be performed in a different order from those described herein. It should be noted that the number and type of diapers within the system and method may vary as long as needs of care givers are considered.

The system and method described herein may facilitate multiple diaper changes per day. The system and method may also reduce the number of steps that are required to change a diaper. It should be noted that the diapers which are within the dispenser may be folded laterally, longitudinally or in any manner that facilitates storing the diapers within the dispenser.

FIGS. 1-12 are representational and are not necessarily drawn to scale. Certain proportions thereof may be exaggerated, while others may be minimized.

While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

We claim:

1. A system for unfolding and dispensing diapers, the system comprising:
    a dispenser having a dispenser opening defined in a side wall of the dispenser, the dispensing opening having end portions at opposite ends of a middle portion, the end portions defined by a respective end wall of the dispensing opening and a respective projection that extends into the dispensing opening towards the end wall, the end portions having a height that is greater than a height of the middle portion of the dispensing opening; and
    a plurality of folded diapers within the dispenser, each folded diaper including longitudinal ends and a first side portion defined between a first longitudinal fold and a main portion and a second side portion defined between the main portion and a second longitudinal fold, the first and second side portions folded along the respective first and second longitudinal folds onto the main portion, the folded diaper disposed within the dispenser such that the first and second side portions are upwardly facing and one of the longitudinal ends is presented at the dispenser opening,
    wherein the dispenser opening has a width inclusive of the end portions equal to a transverse width of the main portion of the folded diaper, a first one of the projections having a length and angular orientation so as to engage the folded diaper between the first side portion and the main portion as the longitudinal end of the diaper is removed from the dispenser and a second one of the projections having a length and angular orientation so as to engage the folded diaper between the second side portion and the main portion as the longitudinal end of the diaper is removed from the dispenser, whereas the first and second side portions unfold upwardly and away from the main portion and into the respective end portions as the folded diaper is pulled through the dispenser opening in the longitudinal direction.

2. The system of claim 1 wherein the dispenser is a disposable package.

3. The system of claim 1 wherein the dispenser is a reusable container.

4. The system of claim 1 wherein the dispenser includes a top wall and a bottom wall, the top and bottom walls being connected together by a plurality of side walls.

5. The system of claim 1 wherein the plurality of folded diapers is part of a roll of folded diapers.

6. The system of claim 1 wherein each folded diaper is connected to another folded diaper by a perforated section that is torn as each diaper is removed from the dispenser.

7. The system of claim 1 wherein the plurality of folded diapers is stacked one on top of another within the dispenser.

8. The system of claim 1 wherein the plurality of folded diapers are interfolded.

* * * * *